(12) United States Patent
Ruggio

(10) Patent No.: US 7,641,608 B1
(45) Date of Patent: Jan. 5, 2010

(54) SECTIONAL CARDIAC SUPPORT DEVICE AND METHOD OF DELIVERY

(75) Inventor: Joseph M Ruggio, Laguna Hills, CA (US)

(73) Assignee: Acorn Cardiovascular, Inc., St. Paul, MN (US)

( * ) Notice: Subject to any disclaimer, the term of this patent is extended or adjusted under 35 U.S.C. 154(b) by 451 days.

(21) Appl. No.: 11/535,251

(22) Filed: Sep. 26, 2006

(51) Int. Cl.
*A61F 2/00* (2006.01)
(52) U.S. Cl. .......................................... 600/37; 600/16
(58) Field of Classification Search .................... 600/37; 604/101.03, 101.05, 509; 606/194; 623/904
See application file for complete search history.

(56) References Cited

U.S. PATENT DOCUMENTS

| | | |
|---|---|---|
| 1,682,119 A | 8/1928 | Field |
| 1,965,542 A | 7/1934 | Colvin, Jr. |
| 1,982,207 A | 11/1934 | Furniss |
| 2,138,603 A | 11/1938 | Johnson |
| 2,278,926 A | 4/1942 | Hartwell |
| 2,376,442 A | 5/1945 | Mehler |
| 2,992,550 A | 7/1961 | Frith |
| 3,384,530 A | 5/1968 | Mercer et al. |
| 3,452,742 A | 7/1969 | Muller |
| 3,551,543 A | 12/1970 | Mercer et al. |
| 3,587,567 A | 6/1971 | Schiff |
| 3,732,662 A | 5/1973 | Paxton |
| 3,768,643 A | 10/1973 | Bruno |
| 3,983,863 A | 10/1976 | Janke et al. |
| 4,048,990 A | 9/1977 | Goetz |
| 4,196,534 A | 4/1980 | Shibamoto |
| 4,403,604 A | 9/1983 | Wilkinson et al. |
| 4,428,375 A | 1/1984 | Ellman |
| 4,466,331 A | 8/1984 | Matheson |
| 4,536,893 A | 8/1985 | Parravicini |
| 4,567,900 A | 2/1986 | Moore |
| 4,630,597 A | 12/1986 | Kantrowitz et al. |
| 4,637,377 A | 1/1987 | Loop |
| 4,690,134 A | 9/1987 | Snyders |
| 4,790,850 A | 12/1988 | Dunn et al. |
| 4,821,723 A | 4/1989 | Baker, Jr. et al. |
| 4,827,932 A | 5/1989 | Ideker et al. |
| 4,834,707 A | 5/1989 | Evans |
| 4,840,626 A | 6/1989 | Linsky et al. |
| 4,878,890 A | 11/1989 | Bilweis |
| 4,932,972 A | 6/1990 | Dunn et al. |

(Continued)

FOREIGN PATENT DOCUMENTS

DE     3 24 524     8/1920

(Continued)

OTHER PUBLICATIONS

"Abstracts From the 68th Scientific Sessions, Anaheim Convention Center, Anaheim, California, Nov. 13-16, 1995", *American Heart Association Supplement to Circulation*, vol. 92, No. 8, Abstracts 1810-1813 (Oct. 15, 1995).

(Continued)

*Primary Examiner*—Charles A Marmor, II
*Assistant Examiner*—Catherine E. Burk
(74) *Attorney, Agent, or Firm*—Faegre & Benson LLP

(57) ABSTRACT

A cardiac support device formed from a plurality of compliant sections individually delivered and deployed at positions around the heart and interconnected to one another.

14 Claims, 3 Drawing Sheets

U.S. PATENT DOCUMENTS

| | | | |
|---|---|---|---|
| 4,936,857 A | 6/1990 | Kulik | |
| 4,957,477 A | 9/1990 | Lundback | |
| 4,973,300 A | 11/1990 | Wright | |
| 4,976,730 A | 12/1990 | Kwan-Gett | |
| 4,995,857 A | 2/1991 | Arnold | |
| 5,042,463 A | 8/1991 | Lekholm | |
| 5,057,117 A | 10/1991 | Atweh | |
| 5,074,129 A | 12/1991 | Matthew | |
| 5,078,681 A * | 1/1992 | Kawashima | 606/198 |
| 5,087,243 A | 2/1992 | Avitall | |
| 5,131,905 A | 7/1992 | Grooters | |
| 5,150,706 A | 9/1992 | Cox et al. | |
| 5,186,711 A | 2/1993 | Epstein | |
| 5,188,813 A | 2/1993 | Fairey et al. | |
| 5,192,314 A | 3/1993 | Daskalakis | |
| 5,207,725 A | 5/1993 | Pinkerton | |
| 5,224,363 A | 7/1993 | Sutton | |
| 5,256,132 A | 10/1993 | Snyders | |
| 5,279,539 A | 1/1994 | Bohan et al. | |
| 5,290,217 A | 3/1994 | Campos | |
| 5,336,253 A | 8/1994 | Gordon et al. | |
| 5,339,657 A | 8/1994 | McMurray | |
| 5,341,815 A | 8/1994 | Cofone et al. | |
| 5,356,432 A | 10/1994 | Rutkow et al. | |
| 5,366,460 A | 11/1994 | Eberbach | |
| 5,383,840 A | 1/1995 | Heilman et al. | |
| 5,385,156 A * | 1/1995 | Oliva | 128/898 |
| 5,405,360 A | 4/1995 | Tovey | |
| 5,409,703 A | 4/1995 | McAnalley et al. | |
| 5,429,584 A | 7/1995 | Chiu | |
| 5,507,779 A | 4/1996 | Altman | |
| 5,524,633 A | 6/1996 | Heaven et al. | |
| 5,533,958 A | 7/1996 | Wilk | |
| 5,558,617 A | 9/1996 | Heilman et al. | |
| 5,593,441 A | 1/1997 | Lichtenstein et al. | |
| 5,603,337 A | 2/1997 | Jarvik | |
| 5,611,515 A | 3/1997 | Benderev et al. | |
| 5,647,380 A | 7/1997 | Campbell et al. | |
| 5,695,525 A | 12/1997 | Mulhauser et al. | |
| 5,702,343 A | 12/1997 | Alferness | |
| 5,713,954 A | 2/1998 | Rosenberg et al. | |
| 5,735,290 A | 4/1998 | Sterman et al. | |
| 5,766,216 A | 6/1998 | Gangal et al. | |
| 5,782,746 A | 7/1998 | Wright | |
| 5,800,334 A | 9/1998 | Wilk | |
| 5,800,528 A | 9/1998 | Lederman et al. | |
| 5,839,842 A | 11/1998 | Wanat et al. | |
| 5,853,422 A | 12/1998 | Huebsch et al. | |
| 5,928,250 A | 7/1999 | Koike et al. | |
| 5,931,810 A | 8/1999 | Grabek | |
| 5,961,440 A | 10/1999 | Schweich, Jr. et al. | |
| 5,972,013 A | 10/1999 | Schmidt | |
| 5,990,378 A | 11/1999 | Ellis | |
| 6,045,497 A | 4/2000 | Schweich, Jr. et al. | |
| 6,050,936 A | 4/2000 | Schweich, Jr. et al. | |
| 6,059,715 A | 5/2000 | Schweich, Jr. et al. | |
| 6,076,013 A | 6/2000 | Brennan et al. | |
| 6,077,214 A | 6/2000 | Mortier et al. | |
| 6,077,218 A | 6/2000 | Alferness | |
| 6,085,754 A | 7/2000 | Alferness et al. | |
| 6,089,051 A | 7/2000 | Goryworda et al. | |
| 6,095,968 A | 8/2000 | Snyders | |
| 6,123,662 A | 9/2000 | Alferness et al. | |
| 6,126,590 A | 10/2000 | Alferness | |
| 6,155,968 A | 12/2000 | Wilk | |
| 6,155,972 A | 12/2000 | Nauertz et al. | |
| 6,165,121 A | 12/2000 | Alferness | |
| 6,165,122 A | 12/2000 | Alferness | |
| 6,169,922 B1 | 1/2001 | Alferness et al. | |
| 6,174,279 B1 | 1/2001 | Girard | |
| 6,179,791 B1 | 1/2001 | Krueger | |
| 6,193,648 B1 | 2/2001 | Krueger | |
| 6,205,747 B1 | 3/2001 | Paniagua Olaechea | |
| 6,206,004 B1 | 3/2001 | Schmidt et al. | |
| 6,224,540 B1 | 5/2001 | Lederman et al. | |
| 6,230,714 B1 | 5/2001 | Alferness et al. | |
| 6,241,654 B1 | 6/2001 | Alferness | |
| 6,293,906 B1 | 9/2001 | Vanden Hoek et al. | |
| 6,360,749 B1 | 3/2002 | Jayaraman | |
| 6,370,429 B1 | 4/2002 | Alferness et al. | |
| 6,375,608 B1 | 4/2002 | Alferness | |
| 6,402,680 B2 | 6/2002 | Mortier et al. | |
| 6,416,459 B1 | 7/2002 | Haindl | |
| 6,425,856 B1 | 7/2002 | Shapland et al. | |
| 6,432,039 B1 | 8/2002 | Wardle | |
| 6,482,146 B1 | 11/2002 | Alferness et al. | |
| 6,508,756 B1 | 1/2003 | Kung et al. | |
| 6,517,570 B1 | 2/2003 | Lau et al. | |
| 6,537,203 B1 | 3/2003 | Alferness et al. | |
| 6,541,678 B2 | 4/2003 | Klein | |
| 6,544,168 B2 | 4/2003 | Alferness | |
| 6,564,094 B2 | 5/2003 | Alferness et al. | |
| 6,567,699 B2 | 5/2003 | Alferness et al. | |
| 6,569,082 B1 | 5/2003 | Chin | |
| 6,572,533 B1 * | 6/2003 | Shapland et al. | 600/37 |
| 6,579,226 B2 | 6/2003 | Vanden Hoek et al. | |
| 6,582,355 B2 | 6/2003 | Alferness et al. | |
| 6,587,734 B2 | 7/2003 | Okuzumi | |
| 6,602,184 B2 | 8/2003 | Lau et al. | |
| 6,612,978 B2 | 9/2003 | Lau et al. | |
| 6,612,979 B2 | 9/2003 | Lau et al. | |
| 6,645,139 B2 | 11/2003 | Haindl | |
| 6,663,558 B2 | 12/2003 | Lau et al. | |
| 6,673,009 B1 | 1/2004 | Vanden Hoek et al. | |
| 6,682,474 B2 | 1/2004 | Lau et al. | |
| 6,682,475 B2 | 1/2004 | Cox et al. | |
| 6,682,476 B2 | 1/2004 | Alferness et al. | |
| 6,689,048 B2 | 2/2004 | Vanden Hoek et al. | |
| 6,695,769 B2 | 2/2004 | French et al. | |
| 6,702,732 B1 | 3/2004 | Lau et al. | |
| 6,723,041 B2 | 4/2004 | Lau et al. | |
| 6,730,016 B1 | 5/2004 | Cox et al. | |
| 6,749,556 B2 * | 6/2004 | Banik | 600/30 |
| 6,755,779 B2 | 6/2004 | Vanden Hoek et al. | |
| 6,881,185 B2 | 4/2005 | Vanden Hock et al. | |
| 6,893,392 B2 | 5/2005 | Alferness | |
| 6,902,522 B1 | 6/2005 | Walsh et al. | |
| 6,902,524 B2 | 6/2005 | Alferness et al. | |
| 6,908,426 B2 | 6/2005 | Shapland et al. | |
| 6,951,534 B2 | 10/2005 | Girard | |
| 7,060,023 B2 | 6/2006 | French et al. | |
| 7,081,086 B2 | 7/2006 | Lau et al. | |
| 7,146,226 B2 * | 12/2006 | Lau et al. | 607/129 |
| 7,155,295 B2 | 12/2006 | Lau et al. | |
| 7,163,507 B2 | 1/2007 | Alferness et al. | |
| 7,189,203 B2 | 3/2007 | Lau et al. | |
| 7,235,042 B2 | 6/2007 | Vanden Hoek et al. | |
| 7,252,632 B2 | 8/2007 | Shapland et al. | |
| 2002/0019580 A1 | 2/2002 | Lau et al. | |
| 2003/0229266 A1 | 12/2003 | Girard et al. | |
| 2004/0059181 A1 | 3/2004 | Alferness | |
| 2004/0143155 A1 * | 7/2004 | Lau et al. | 600/37 |
| 2005/0033109 A1 | 2/2005 | Lau et al. | |
| 2005/0059854 A1 | 3/2005 | Vanden Hoek et al. | |
| 2005/0059855 A1 | 3/2005 | Lau et al. | |
| 2005/0090707 A1 | 4/2005 | Lau et al. | |
| 2005/0171589 A1 | 8/2005 | Lau et al. | |
| 2005/0192474 A1 | 9/2005 | Vanden Hoek et al. | |
| 2005/0256368 A1 | 11/2005 | Klenk et al. | |
| 2005/0288715 A1 | 12/2005 | Lau et al. | |
| 2006/0009831 A1 | 1/2006 | Lau et al. | |
| 2006/0229490 A1 | 10/2006 | Chin | |
| 2006/0270896 A1 | 11/2006 | Dietz et al. | |
| 2007/0208211 A1 | 9/2007 | Alferness et al. | |

| | | | |
|---|---|---|---|
| 2007/0219407 | A1* | 9/2007 | Vanden Hoek et al. ........ 600/37 |
| 2007/0225547 | A1 | 9/2007 | Alferness et al. |
| 2008/0021266 | A1* | 1/2008 | Laham et al. ................. 600/37 |

FOREIGN PATENT DOCUMENTS

| | | |
|---|---|---|
| DE | 38 31 540 | 4/1989 |
| DE | 295 17 393 | 3/1996 |
| EP | 0 280 564 | 8/1988 |
| EP | 0 303 719 | 2/1989 |
| EP | 0 557 964 | 9/1993 |
| GB | 2 209 678 | 5/1989 |
| JP | 60-203250 | 10/1985 |
| JP | 01-145066 | 6/1989 |
| JP | 2-271829 | 11/1990 |
| SU | 1009457 | 4/1983 |
| WO | WO 93/03685 | 3/1993 |
| WO | WO 96/16601 | 6/1996 |
| WO | WO 96/31175 | 10/1996 |
| WO | WO 98/14136 | 4/1998 |
| WO | WO 98/29041 | 7/1998 |
| WO | WO 98/35632 | 8/1998 |
| WO | WO 98/58598 | 12/1998 |
| WO | WO 99/44534 | 9/1999 |
| WO | WO 00/02500 | 1/2000 |
| WO | WO 00/06026 | 2/2000 |
| WO | WO 00/06027 | 2/2000 |
| WO | WO 00/06028 | 2/2000 |
| WO | WO 00/16700 | 3/2000 |
| WO | WO 01/02500 | 1/2001 |
| WO | WO 01/67985 | 9/2001 |
| WO | WO 2006/023580 | 3/2006 |

OTHER PUBLICATIONS

Capomolla et al., "Dobutamine and nitroprusside infusion in patients with severe congestive heart failure: Hemodynamic improvement by discordant effects on mitral regurgitation, left atrial function, and ventricular function", *American Heart Journal*, pp. 1089-1098 (Dec. 1997).

Capouya et al., "Girdling Effect of Nonstimulated Cardiomyoplasty on Left Ventricular Function", *The Society of Thoracic Surgeons*, vol. 56, pp. 867-871 (1993).

Cohn, "The Management of Chronic Heart Failure", *The New England Journal of Medicine*, vol. 335, No. 7, pp. 490-498 (Aug. 15, 1996).

Colleta et al., "Prognostic value of left ventricular volume response during dobutamine stress echocardiography", *European Heart Journal*, vol. 18, pp. 1599-1605 (Oct. 1997).

deVries, G. et al., "A Novel Technique for Measurement of Pericardial Balloon," *Am. J. Physiol Heart Circ Physiol*, vol. 280, No. 6, pp. H2815-H2822 (Jan. 2001).

Guasp, "Una protesis contentiva pare el tratamiento de la miocardiopatia dilatada" *Revista Espanola de Cardiologia*, vol. 51, No. 7, pp. 521-528 (1998). (Includes the English translation).

Hamilton, D. et al., "Static and Dynamic Operating Characteristics of a Pericardial Balloon," *J. Appl. Physiol.*, vol. 90, No. 4, pp. 1481-1488 (Apr. 2001).

Kass et al., "Reverse Remodeling From Cardiomyoplasty in Human Heart Failure", *Circulation*, vol. 91, No. 9, pp. 2314-2318 (May 1, 1995).

Labrousse, et al., "Implantation of a Cardiac Support Device by the 'Parachute-Like' Technique through Sternal and Trans-Abdominal Approach", *Hopital Haut Bordeaux University Hospital, France; Lenox Hill Hospital New York, United States*.

Levin et al., "Reversal of Chronic Ventricular Dilation in Patients With End-Stage Cardiomyopathy by Prolonged Mechanical Unloading", *Circulation*, vol. 91, No. 11, pp. 2717-2720 (Jun. 1, 1995).

Oh et al., "The Effects Of Prosthetic Cardiac Binding And Adynamic Cardiomyoplasty In A Model Of Dilated Cardiomyopathy", *The Journal of Thoracic and Cardiovascular Surgery*, vol. 116, No. 1, pp. 148-153 (Jul. 1998).

Paling, "Two-Bar Fabrics (Part-Set Threading)", *Warp Knitting Technology*, Columbine Press (Publishers) Ltd., Buxton, Great Britain, p. 111 (1970).

Vaynblat et al., "Cardiac Binding in Experimental Heart Failure", *Ann Thorac Surg*, Vol. 64 (1997).

Vinereanu, et al., "Worsening Global Diastolic Dysfunction of the Left Ventricle is Associated with a Progressive Decline in Longitudinal Systolic Function", *European Journal of Heart Failure*, Aug 7(5): 820-8 (2005).

U.S. Appl. No. 60/148,130 entitled, "Apparatus and Method for Endoscopic Pericardial Access", filed Aug. 10, 1999.

U.S. Appl. No. 60/150,737 entitled, "Longitudinal Mechanical Dilator for Vessel Harvesting", filed Aug. 25, 1999.

U.S. Appl. No. 09/635,345 entitled, "Apparatus and Methods for Subxiphoid Endoscopic Access", filed Aug. 9, 2000.

* cited by examiner

SECTIONAL CARDIAC SUPPORT DEVICE AND METHOD OF DELIVERY

FIELD OF THE INVENTION

The present invention is a cardiac support device and associated delivery tool and deployment method.

BACKGROUND OF THE INVENTION

Cardiac support devices for treating congestive heart failure are known. One such cardiac support device includes a compliant and sometimes elastic jacket for reducing tension in the heart wall by constraining or resisting expansion of the heart. Tools and methods for delivering cardiac support devices using minimally invasive surgical procedures are also known. Cardiac support devices of these types and associated delivery tools and methods are described, for example, in the following U.S. patents and published applications, all of which are incorporated herein by reference in their entirety: U.S. Pat. Nos. 5,702,343, 6,155,972, 6,193,648, 6,293,906, 6,482,146, 6,682,476, 6,902,524, 6,425,856, 6,908,426, 6,572,533, 6,951,534, 6,702,732, 6,723,041, 2006/0009831, 2005/0288715, 2005/0256368, 2005/0171589, 2005/0090707, 2005/0059854 and 2005/0059855.

There remains, however, a continuing need for improved cardiac support devices and related delivery tools and methods. In particular, there is a need for devices, tools and methods of these types that can be used in connection with minimally invasive surgical procedures.

SUMMARY OF THE INVENTION

The present invention is an improved cardiac support device and a delivery tool that can be used to mount the support device on the patient during a minimally invasive surgical procedure. One embodiment of the invention includes placing a plurality of compliant cardiac support device sections around at least a portion of a lower portion of a heart and interconnecting the compliant sections to form the cardiac support device. The compliant sections can be balloon-rupturable members that are adhesively interconnected to one another.

DETAILED DESCRIPTION OF THE PREFERRED EMBODIMENTS

Figure 1:
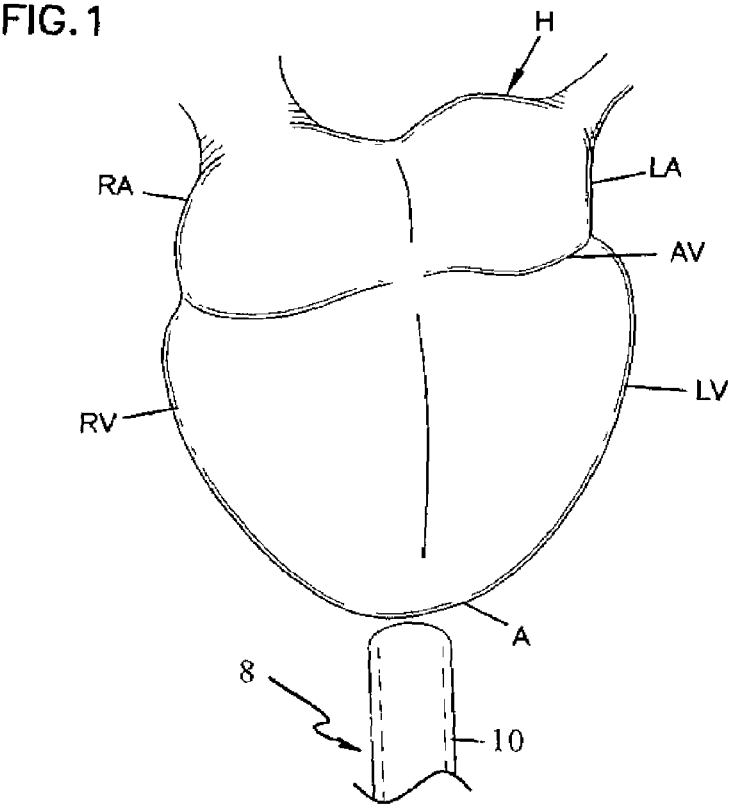
FIG. 1 is an illustration of a delivery device in accordance with one embodiment of the present invention positioned adjacent to the apex of the heart.

FIG. 1 is an illustration of the distal portion of a delivery tool or device 8 including a balloon section 12a of a cardiac support device in accordance with the present invention positioned adjacent to the apex A of a heart H. As shown, the heart H also has a right atrium RA, left atrium LA, right ventricle RV and left ventricle LV. The ventricles RV and LV are generally separated by the atrioventricular (AV) groove AV. In the illustrated embodiment the delivery device 8 includes a tubular sheath 10 that surrounds at least a portion of the cardiac support device balloon section 12a. The cardiac support device section 12a is an inverted balloon, and is shown in an undeployed, collapsed form in FIG. 1.

Access of the delivery device 8 to the epicardial space and heart H can be obtained through a sub-xiphoid or similar approach. Using conventional techniques, for example, a needle (e.g., 16-gauge or 18-gauge) (not shown) would enter the intrapericardial space using an alligator clamp for ECG monitoring. Once in the pericardial space the needle can be used for the insufflation of a gas such as carbon dioxide. Insufflation of gas permits definition of the anatomy with stark contrast both by fluoroscopy and echocardiographic imaging approaches. For example, this approach will provide a true space separating the visceral pericardium from the parietal pericardium. Clear identification of the left ventricle and surrounding structures such as the apex A of heart H can be achieved. Other advantages include efficacious and safe access to the intrapericardial space and potentially reduced ventricular ectopy and coronary artery trauma. Furthermore, this action facilitates the efficient insertion of the sheath 10 and deployment of the balloon section 12a.

The distal end of the sheath 10 is then advanced toward the heart H, and is preferably located adjacent to the apex A as shown in FIG. 1. If needed or otherwise appropriate, structures and methods can be used to secure the delivery device 8 to the apex A of the heart H. Suction-tike devices and screw-like devices can, for example, be used for this purpose. Securing the apex A of the heart H in this manner may be particularly advantageous in connection with the coaxial deployment of delivery device 8.

After the sheath 10 is properly positioned, the uninflated balloon section 12a of the cardiac support device is deployed by advancing or otherwise removing that section from the sheath and locating the section adjacent to the side of the heart H. In the illustrated embodiment the balloon section 12a is advanced from the distal end of the sheath 10. However, in other embodiments (not shown) other structures and methods are used to position the balloon section 12a adjacent to the heart H.

Figure 2:
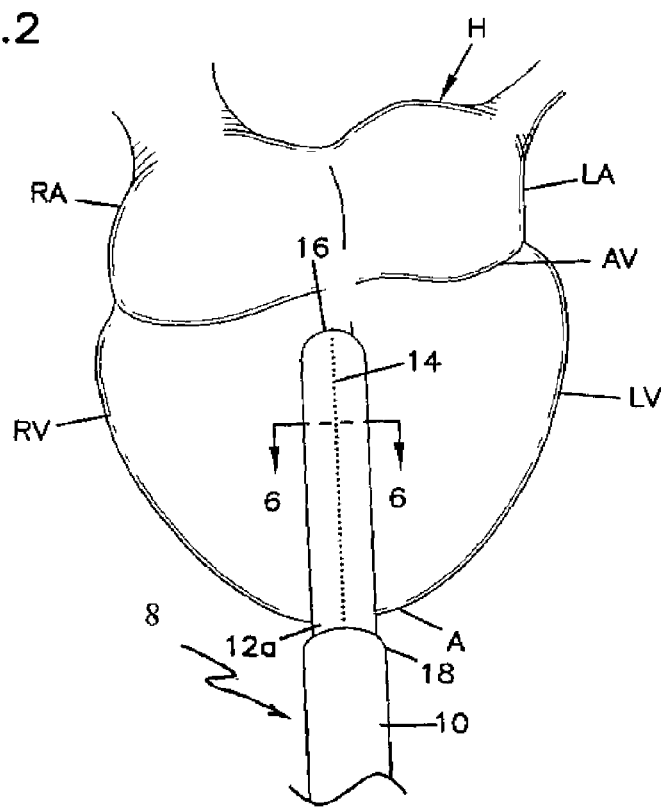
FIG. 2 is an illustration of the delivery device and heart shown in FIG. 1, with the cardiac support device inserted but undeployed or partially deployed from the delivery device.

As shown in FIG. 2, balloon section 12a has a score line 14 extending in a generally longitudinal direction with respect to the heart H. Score line 14 is a structure that facilitates the controlled breakage or rupture of the balloon section 12a into sheaves (e.g., segments that can be flattened). Other structures or approaches (not shown) are used for this purpose in other embodiments.

Figure 3:
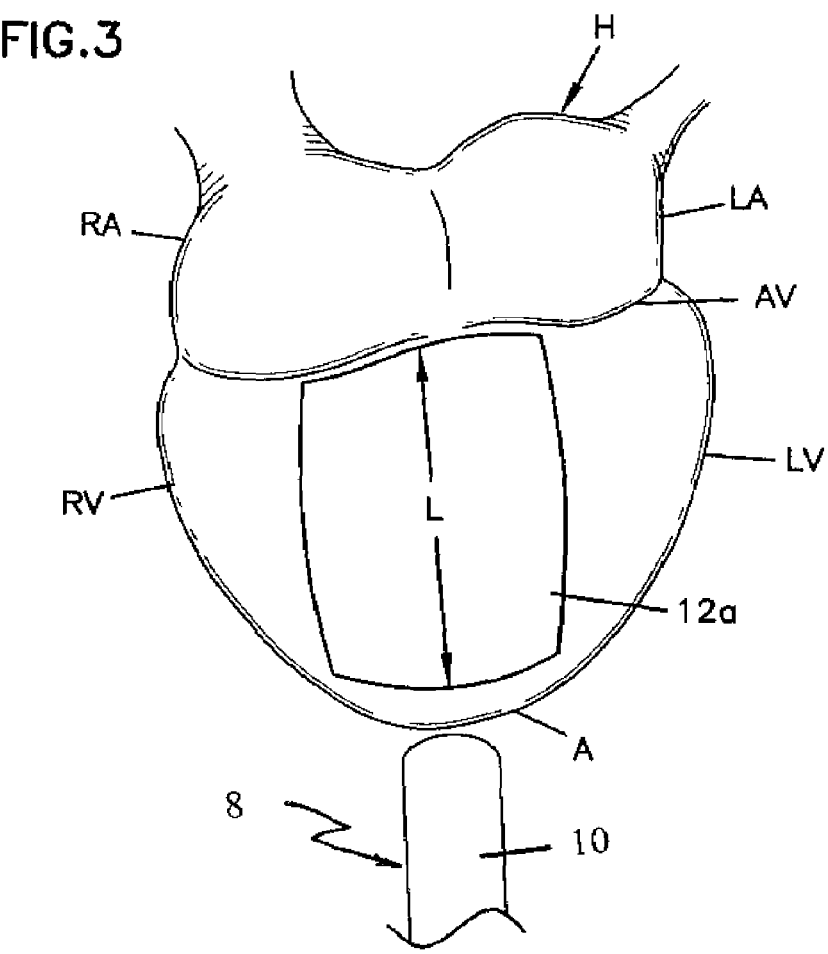
FIG. 3 is an illustration of the delivery device and heart shown in FIG. 1, with a section of the cardiac support device deployed and placed on the surface of the heart.
Figure 6:
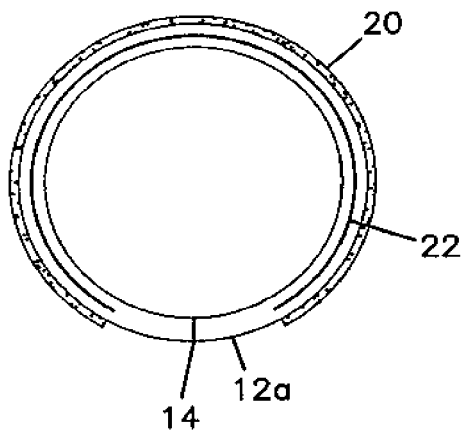
FIG. 6 is a cross sectional view take at line 6-6 in FIG. 2, showing the cardiac support device partially deployed from the delivery device.

Balloon section 12a is inflated by a source of pressurized gas after it is positioned relative to the heart H to continue the deployment process. FIG. 6 is a cross sectional illustration of balloon section 12a during inflation. With continued inflation the balloon section 12a will rupture at a predetermined inflation pressure along the score line 14. This action causes the balloon section 12a to take on a generally flat, panel-shaped configuration overlaying a portion of the heart H as shown in FIG. 3. In the deployed position shown in FIG. 3 the balloon section 12a will overlie a portion of the heart H between the AV groove AV and the apex A. Radiopaque elements or portions (not shown) on the balloon sections 12a can be used in connection with fluoroscopic or other imaging approaches to locate and orient the balloon sections on the heart and relative to other structures.

The balloon section 12a can be formed from materials that take the panel-shaped configuration upon deployment (e.g., composites). Alternatively, additional elements such as shape memory elements or resilient members (not shown) can be can be incorporated on the balloon sections 12a to bias the balloon sections to the desired configuration upon deployment. These additional elements can be permanently mounted to the balloon sections 12a, or temporarily mounted thereto and removed following deployment.

Figure 4:
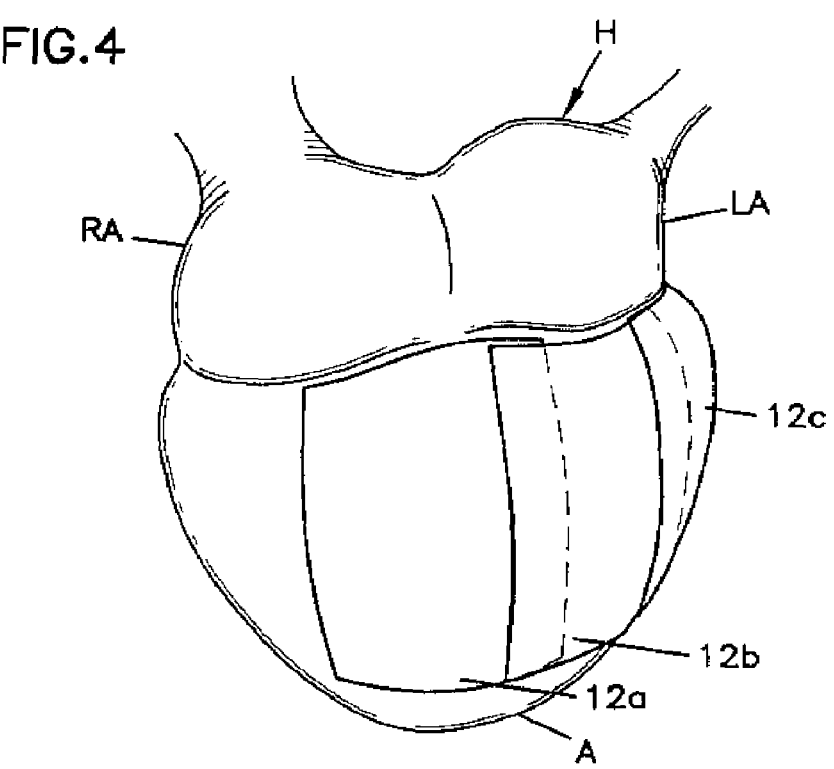
FIG. 4 is an illustration of the heart shown in FIG. 2 with several sections of the cardiac support device placed on the heart.
Figure 5:
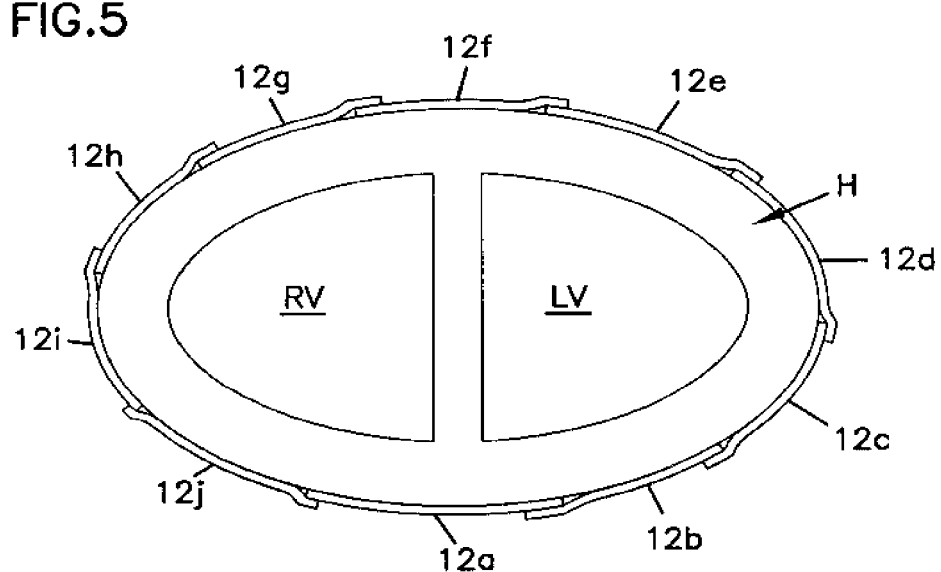
FIG. 5 is a cross section of an inferior, near apical portion of a heart with a cardiac support device in accordance with the invention positioned on the heart.

Additional balloon sections such as 12b and 12c shown in FIG. 4 are then deployed around all or portions of the heart H in a manner similar to that described above. Additional balloon sections (e.g., 12b and 12c) can be advanced out of the sheath 10 that was used to deploy balloon section 12a. Alternatively, sheath 10 can be withdrawn and additional sheaths containing the additional balloon sections (not shown) can be used for this purpose. As shown in FIG. 4, balloon sections 12a-12c overlap one another. The balloon segments 12-12c can include structure for causing the overlapping portions of the segments to join together. In the embodiment illustrated in FIG. 6, for example, the segments 12a-12c include a layer of adhesive 20 on the side of the segments facing the heart H. The overlapping portions of the segments 12a-12c are then secured together by the adhesive. Other structures and approaches can also be used to join the balloon sections 12a-12c, and the adjacent edges of the sections need not overlap. For example, the adhesive 20 could be located on the opposite side of the balloon sections 12a-12c and/or only on the edges. FIG. 5 is a cross sectional illustration of heart H with a completed cardiac support device in accordance with the invention formed from joined segments 12a-12j that surround the lower portion of the heart.

Resilient elements or other structures and methods can be used to cause the balloon sections 12a-12j to flatten and lie adjacent to the side of the heart H following deployment. In the embodiment shown in FIG. 6, for example, the balloon segment 12a includes a nitinol spring element 22 that will bias to the balloon segment to a flattened state after deployment.

Balloon segments such as 12a-12j are formed from materials that cause the cardiac support device to have characteristics (e.g., compliance and elasticity) that can vary and provide the therapeutic benefits of the cardiac support devices described in the background section of this document. As a non-limiting example, materials of the types used for commercially-available balloon-deployable stents can be used for this device. Although not shown, additional structures such as nitinol mesh that have compliances or other characteristics that contribute to the therapeutic functionality of the cardiac support device can be incorporated onto the balloon segments 12a-12j.

The invention offers a number of important advantages. In addition to providing the therapeutic effects of a cardiac support device, it can be efficiently and effectively implanted on a patient's heart using noninvasive surgical procedures.

Although the present invention has been described with reference to preferred embodiments, those skilled in the art will recognize that changes can be made in form and detail without departing from the spirit and scope of the invention. For example, cardiac support devices in accordance with the present invention that are assembled from segments can take other forms and be deployed by other approaches.

What is claimed is:

1. A method for delivering a cardiac support device to a patient, including:
    placing a plurality of compliant and rupturable cardiac support device sections in an undeployed state adjacent to a side of a lower portion of a heart; and
    deploying the device sections by acting on the sections and causing the device sections to rupture and expand to a generally flattened state; and
    interconnecting the deployed device sections to form a cardiac support device.

2. The method of claim 1 wherein each of the sections is separately delivered and placed on the heart.

3. The method of claim 1 wherein edges of the compliant sections overlap.

4. The method of claim 1 wherein interconnecting the compliant sections includes adhesively interconnecting the sections.

5. The method of claim 1 wherein interconnecting the compliant sections includes mechanically interconnecting the sections.

6. The method of claim 1 including placing and interconnecting compliant sections around an entire lower portion of the heart.

7. The method of claim 1 wherein deploying the device sections includes inflating undeployed sections with gas and forcing the sections to rupture.

8. The method of claim 1 wherein deploying the device sections includes mechanically acting on the undeployed sections to cause the sections to rupture.

9. The method of claim 1 wherein deploying the sections includes causing the sections to self-expand.

10. The method of claim 1 performed by minimally invasive surgical techniques.

11. The method of claim 1 and further including insufflating a pericardial space around the patient's heart with gas before placing and interconnecting the sections.

12. A system for deploying a cardiac support device, comprising:
    a plurality of compliant and rupturable sections in an undeployed state configured to be interconnected with other compliant and rupturable sections in an undeployed state to form a cardiac support device; and
    a delivery means for holding the one or more compliant sections in the undeployed state for insertion into a pericardial space adjacent a heart, and including a deployment means for rupturing the sections and causing the compliant sections to take a generally flattened deployed configuration at which they can be interconnected to one another around the heart.

13. The system of claim 12 wherein:
    the compliant sections include balloon segments sections; and
    the deployment means includes a source of pressurized gas for rupturing the compliant sections.

14. The system of claim 12 wherein the compliant sections further include elements for biasing the sections from the collapsed state to the deployed configuration.

* * * * *

UNITED STATES PATENT AND TRADEMARK OFFICE
CERTIFICATE OF CORRECTION

| | | |
|---|---|---|
| PATENT NO. | : 7,641,608 B1 | |
| APPLICATION NO. | : 11/535251 | |
| DATED | : January 5, 2010 | |
| INVENTOR(S) | : Joseph M. Ruggio | |

It is certified that error appears in the above-identified patent and that said Letters Patent is hereby corrected as shown below:

Column 4, line 50, after "the" and before "compliant" delete "one or more"

Column 4, line 58, after "balloon segments" delete "sections"

Signed and Sealed this

Fourth Day of May, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,641,608 B1 | Page 1 of 1 |
| APPLICATION NO. | : 11/535251 | |
| DATED | : January 5, 2010 | |
| INVENTOR(S) | : Joseph M. Ruggio | |

It is certified that error appears in the above-identified patent and that said Letters Patent is hereby corrected as shown below:

On the title page, change Notice to read as follows:

(*) Notice:    Subject to any disclaimer, the term of this Patent is extended or adjusted under 35 U.S.C. 154(b) 552 days.

Signed and Sealed this

Twenty-ninth Day of June, 2010

David J. Kappos
*Director of the United States Patent and Trademark Office*